US007943604B2

(12) United States Patent
Coelingh Bennink et al.

(10) Patent No.: US 7,943,604 B2
(45) Date of Patent: May 17, 2011

(54) METHOD OF TREATING HUMAN SKIN AND A SKIN CARE COMPOSITION FOR USE IN SUCH A METHOD

(75) Inventors: Herman Jan Tijmen Coelingh Bennink, Driebergen (NL); Evert Johannes Bunschoten, Heesch (NL); Christian Franz Holinka, New York, NY (US)

(73) Assignee: Pantarhei Bioscience B.V. (NL)

( * ) Notice: Subject to any disclaimer, the term of this patent is extended or adjusted under 35 U.S.C. 154(b) by 690 days.

(21) Appl. No.: 10/517,509

(22) PCT Filed: Jun. 11, 2003

(86) PCT No.: PCT/NL03/00420
§ 371 (c)(1),
(2), (4) Date: Jun. 13, 2005

(87) PCT Pub. No.: WO03/103685
PCT Pub. Date: Dec. 18, 2003

(65) Prior Publication Data
US 2005/0215538 A1    Sep. 29, 2005

(30) Foreign Application Priority Data

Jun. 11, 2002 (EP) .................................. 02077273

(51) Int. Cl.
*A61K 31/56* (2006.01)
*A61K 8/02* (2006.01)
(52) U.S. Cl. ........................................ 514/182; 424/401
(58) Field of Classification Search .................. 514/182; 424/401
See application file for complete search history.

(56) References Cited

U.S. PATENT DOCUMENTS

| 3,440,320 | A | | 4/1969 | Sackler et al. |
| 3,797,494 | A | | 3/1974 | Zaffaroni |
| 4,460,372 | A | | 7/1984 | Campbell et al. |
| 4,573,996 | A | | 3/1986 | Kwiatek et al. |
| 4,624,665 | A | | 11/1986 | Nuwayser |
| 4,722,941 | A | | 2/1988 | Eckert et al. |
| 4,762,717 | A | | 8/1988 | Crowley, Jr. |
| 4,937,238 | A | | 6/1990 | Lemon |
| 5,130,137 | A | | 7/1992 | Crowley, Jr. |
| 5,211,952 | A | * | 5/1993 | Spicer et al. ............... 424/426 |
| 5,223,261 | A | | 6/1993 | Nelson et al. |
| 5,340,584 | A | | 8/1994 | Spicer et al. |
| 5,340,585 | A | | 8/1994 | Pike et al. |
| 5,340,586 | A | | 8/1994 | Pike et al. |
| 5,468,736 | A | | 11/1995 | Hodgen |
| 5,633,242 | A | | 5/1997 | Oettel et al. |
| 5,662,927 | A | | 9/1997 | Ehrlich et al. |
| 5,827,843 | A | | 10/1998 | Koninckx |
| 6,214,815 | B1 | | 4/2001 | Shangold et al. |
| 6,500,814 | B1 | | 12/2002 | Hesch |
| 2002/0183299 | A1 | | 12/2002 | Voskuhl |
| 2004/0192598 | A1 | * | 9/2004 | Kragie ........................... 514/12 |

FOREIGN PATENT DOCUMENTS

| DE | 2336433 A1 | 4/1975 |
| DE | 2336434 A1 | 4/1975 |
| DE | 2426779 A1 | 12/1975 |
| DE | 19917930 A1 | 10/2000 |
| EP | 0402950 A1 | 12/1975 |
| EP | 468690 A1 | 7/1991 |
| EP | 1700602 A1 | 5/2001 |
| WO | 9218107 A1 | 10/1992 |
| WO | 9426207 | 11/1994 |
| WO | 9502408 A1 | 1/1995 |
| WO | 9517895 | 7/1995 |
| WO | 9603929 A1 | 2/1996 |
| WO | 9858657 A1 | 12/1998 |
| WO | 0073416 A1 | 12/2000 |
| WO | 0130357 A | 5/2001 |
| WO | 0185154 A2 | 11/2001 |
| WO | WO 03/018026 | 3/2003 |

OTHER PUBLICATIONS

Webster Ninth New Collegiate Dicitionary, 2000, Definition of Prevention, p. 1.*
Willhite et al. Pharmacotherapy, 2001, vol. 21, Issue 4, pp. 464-480.*
Sitruk-Ware, English Translation, 1997. Praxis, Schweirzerische Rundschau fur Medizin, vol. 86, No. 33, pp. 1-13.*
Younglai et al. Journal of Clinical Endocrinology and Metabolism, 1968, vol. 28, Issue 11, pp. 1611-1617.*
Holinka et al. In vivo Effects of Estetrol on the Immature Rat Uterus. Biology of Reproduction 1979, vol. 20, pp. 242-246.*
Mueck et al., "Angio and Anti-Angiogenetic Effects of Estradiol and its Metabolites", J. Clin. Basic Cardiol., 2001, pp. 153-155, vol. 4, No. 2.
Shah et al., "Estrogen and Skin. An Overview", Am. J. Clin. Dermatol., 2001, pp. 143-150, vol. 2, No. 3.
Sitruk-Ware et al., "Local Hormonal Treatment for Urogenital Atrophy After Menopause", Shweiz. Rundsch, Med. Praxis, 1997, pp. 1245-1248, vol. 86, No. 33.

(Continued)

*Primary Examiner* — Sreeni Padmanabhan
*Assistant Examiner* — Samira Jean-Louis
(74) *Attorney, Agent, or Firm* — The Webb Law Firm

(57) ABSTRACT

The invention relates to cosmetic methods of treating human skin. The method includes applying to the skin a composition containing an estrogenic component and a cosmetically acceptable vehicle. Other aspects of the invention relate to therapeutic methods of treating or preventing vaginal dryness or acne and a therapeutic method of promoting wound healing. Another aspect relates to a skin care composition comprising the aforementioned estrogenic component and a cosmetically acceptable vehicle.

5 Claims, No Drawings

OTHER PUBLICATIONS

Schmidt et al., "Treatment of Skin Aging with Topical Estrogens", Int. J. Dermatol., 1996, pp. 669-674, vol. 35, No. 9.
National Institute of Child Health and Human Development, NIH Publication No. 02-2413 retrieved online on Aug. 9, 2007.
Breast Cancer Prevention retrieved online Aug. 7, 2007 from the internet; http://www.cancer.gov/cancertopics/pdq/prevention/breast/Patient/page 3.
Prophylactic definition—Medical Dictionary of Popular Medical Terms; retrieved on Mar. 14, 2008 via www.medterms.com/script/main/art.asp?articlekey+11902.
Zips et al., in vivo, 2005, vol. 19, pp. 1-8.
Holinka et al., Biology of Reproduction, 1980, vol. 22, pp. 913-926.
Martucci et al., "Impact of Continuously Administered Catechol Estrogens on Uterine Growth and Luteinizing Hormone Secretion", Endocrinology (Dec. 1979), vol. 105, No. 6, pp. 1288-1292.
Weigert et al., "Comparison of Stimulation with Clomiphenes Citrate in Combination with Recombinant Follicle Stimulating Hormone and Recombinant Luteinizing Hormone to Stimulation with a Gonadotropin-Releasing Hormone Agonist Protocol: A Prospective Randomized Study", Fertility and Sterility, (Jul. 2002), vol. 78, No. 1, pp. 34-39.
Trotter et al., "Effects of Postnatal Estradiol and Progesterone Replacement in Extremely Preterm Infants", J. Clin. Endocrinol Metab., (Dec. 1999), vol. 84, No. 12, pp. 4531-4535.
Shanklin et al., "Aqueous Estrogens in the Management of Respiratory Distress SYndrome", J. Reprod. Med. (Aug. 1970), vol. 5, No. 2, pp. 53-71.
Chemical Abstracts Service, Columbus Ohio, US: Jakowicki, "Evaluation of Estriol Level in the Amniotic Fluid in Prolonged Pregnancy", XP002458625, 1979.
Gorwill et al., "Unconjugated Serum Oestriol Levels in Mother and Baby with Meconium Staining of the Amniotic Fluid", Br. J. Obstet. Gynaecol. (Aug. 1978), vol. 85, No. 8, pp. 602-604.
Fogary, Jr., "Postmaturity", J. Am. Osteopath. Assoc., (Jan. 1976), vol. 75, No. 5, pp. 512-517.
Office Action mailed on Jan. 11, 2008 in U.S. Appl. No. 10/478,262.
Office Action mailed on May 15, 2008 in U.S. Appl. No. 10/478,262.
Office Action mailed on Feb. 19, 2009 in U.S. Appl. No. 10/478,262.
Office Action mailed on Jun. 9, 2009 in U.S. Appl. No. 10/478,262.
Office Action mailed on Nov. 18, 2008 in U.S. Appl. No. 10/478,264.
Office Action mailed on May 22, 2009 in U.S. Appl. No. 10/478,264.
Office Action mailed on Mar. 17, 2008 in U.S. Appl. No. 10/478,357.
Office Action mailed on May 16, 2008 in U.S. Appl. No. 10/478,357.
Office Action mailed on Dec. 16, 2008 in U.S. Appl. No. 10/478,357.
Office Action mailed on May 28, 2009 in U.S. Appl. No. 10/478,357.
Office Action mailed on Apr. 6, 2007 in U.S. Appl. No. 10/478,365.
Office Action mailed on Sep. 7, 2007 in U.S. Appl. No. 10/478,365.
Office Action mailed on Apr. 1, 2008 in U.S. Appl. No. 10/478,365.
Office Action mailed on Jun. 8, 2009 in U.S. Appl. No. 10/478,365.
Office Action mailed on Jan. 24, 2007 in U.S. Appl. No. 10/495,707.
Office Action mailed on Dec. 28, 2007 in U.S. Appl. No. 10/495,707.
Office Action mailed on Aug. 19, 2008 in U.S. Appl. No. 10/495,707.
Office Action mailed on May 22, 2009 in U.S. Appl. No. 10/495,707.
Office Action mailed on Aug. 9, 2007 in U.S. Appl. No. 10/517,686.
Office Action mailed on Apr. 4, 2008 in U.S. Appl. No. 10/517,686.
Office Action mailed on May 29, 2009 in U.S. Appl. No. 10/517,686.
Office Action mailed on Apr. 23, 2007 in U.S. Appl. No. 10/521,040.
Office Action mailed on Aug. 17, 2007 in U.S. Appl. No. 10/521,040.
Office Action mailed on Apr. 2, 2008 in U.S. Appl. No. 10/521,040.
Office Action mailed on Jun. 1, 2009 in U.S. Appl. No. 10/521,040.
Visser et al., "In vitro effects of estetrol on receptor binding, drug targets and human liver cell metabolism," Climacteric (2008) 11(1) Appx. II: 1-5.
Visser et al., "First human exposure to exogenous single-dose oral estetrol in early postmenopausal women," Climacteric (2008) 11(1): 1-10.
Visser et al., "Clinical applications of estetrol," J. of Steroid Biochem and Molecular Biol. (2009) 114: 85-89.
Holinka et al., "Estetrol: A unique steroid in human pregnancy," J. of Steroid Biochem and Molecular Biol. (2009) 110: 138-143.
Coelingh Bennink et al., "Oral bioavailability and bone sparing effects of estetrol in an osteoporosis model," Climacteric (2008) 11 (Supp 3): 1-13.
Albertazzi Paola et al., "The Effect of Tibolone Versus Continuous Combined Norethisterone Acetate and Oestradiol on Memory, Libido and Mood of Postmenopausal Women: A Pilot study"; Database Biosis 'Onlinel; Oct. 31, 2000; pp. 223-229; vol. 36, No. 3; Biosciences Information Service, Philadelphia, PA., U.S.
Allen et al., An Ovarian Hormone: Preliminary Report on Its Localization, Extraction and Partial Purification, and Action in Test Animals, JAMA, Sep. 8, 1923, vol. 81, pp. 819-821.
Allen et al., The Induction of a Sexually Mature Condition in Immature Females by Injection of the Ovarian Follicular Hormone, Am. J. Physiol., 1924, vol. 69, pp. 577-588.
Jones et al, The Effects of Various Steroids on the Vaginal Histology in the Rat, Fertility and Sterility, Apr. 1973, vol. 24, No. 4, pp. 284-291.
Tulchinsky et al., Plasma Esterol as an Index of Fetal Well-Being, J. Clin. Endrocrinol. Metab., 1975, vol. 40. pp. 560-567.
Jozan et al., Different Effects of Oestradiol, Oestriol, Oestrol and of Oestrone on Human Breast Cancer Cells (MCF-7) in Long Term Tissue Culture, Acta Endocrinologica, 1981, vol. 98, pp. 73-80.
Hammond et al., A Versatile Method for the Determination of Serum Cortisol Binding Globulin and Sex Hormone Binding Globulin Binding Capacities, 1983, vol. 132, pp. 101-110.
Elger et al., Sulfamates of Various Estrogens are Prodrugs with Increased Systemic and Reduced Hepatic Estrogenicity at Oral Application, J. Steroid Biochem. Molec. Biol., 1995, vol. 55, No. 3 / 4, pp. 395-403.
Murphy et al., Endometrial Effects of Long-Term Low-Dose Administration of RU486, Fertility and Sterility, Apr. 1995, vol. 63, No. 4, pp. 761-766.
Reel et al., Survey and Assessment of Mammalian Estrogen Biological Assays for Hazard Characterization, Fundamental and Applied Toxicology, 1996, vol. 34, pp. 288-305.
Beral et al., Use of HRT and the Subsequent Risk of Cancer, Journal of Epidemiology and Biostatistics, 1999, vol. 4, No. 3, pp. 191-215.
Tavani et al., The Adverse Effects of Hormone Replacement Therapy, Drugs & Aging, May 1999, vol. 14, No. 5, pp. 347-357.
Pike et al., Progestins and Menopause: Epidemiological Studies of Risks of Endometrial and Breast Cancer, Steroids, 2000, vol. 65, pp. 359-664.
Avvakumov et al., Steroid-binding Specificity of Human Sex Hormon-binding Globulin Is Influenced by Occupancy of a Zinc-binding Site, The Journal of Biological Chemistry, Aug. 25, 2000, vol. 275, No. 34, pp. 25920-25925.
Holinka et al., "In Vivo Effects of Esterol on the Immature Rat Uterus", Biology of Reproduction, Society for the Reproduction Society for the Study of Reproduction, Champaign, IL, US, Mar. 1979, vol. 20, No. 2, pp. 242-246.
Holinka, et al., "Comparison of Effects of Esterol and Tamoxifen with Those of Estriol and Estradiol on the Immature Rat Uterus", Biology of Reproduction, Society for the Reproduction Society for the Study of Reproduction, Champaign, IL, US, 1980, vol. 22, No. 4, pp. 913-926.
Jansson et al., "Estrogen Induces a Potent Suppression of Experimental Autoimmune Encephalomyelitis and Collagen-Induced Arthritis in Mice", Journal of Neuroimmunology, Elsevier Science Publishers BV XX, 1994, vol. 53, No. 2, pp. 203-207.
Erdbruegger et al., Drug Discovery Today: Disease Mechanisms (2004), vol. 1, pp. 73-81.
Lab Tests Online (www.labtestsonline.org/understanding/conditions/autoimmune.html) retrieved onOct. 15, 2009.
www.tiscali.co.uk/lifestyle/healthfitness/health_advice/netdoctor/archive/000489.html, retrieved onOct. 15, 2009.
MedlinePlus Medical Encyclopedia: Mutiple Sclerosis, retrieved on Mar. 28, 2008 via www.nlm.nih.gov/medlineplus/ency/article/000737.htm, dated on 0806/2007, p. 1 and 2; also see WebMD: Multiple Sclerosis—Prevention, retrieved on Mar. 28, 2008 via www.webmd.com/multiple-sclerosis/tc/multiple-sclerosis-ms-prevention, dated on Mar. 23, 2006.
MedlinePlus Medical Encyclopedia: rheumatoid arthritis, retrieved on Mar. 28, 2008 via www.nlm.nih.gov/medlineplus/ency/article/

000431.htm, dated on Jul. 27, 2007, p. 1-2 and 4; also WebMD: Rheumatoid Arthritis—Prevention, retrieved on Mar. 28, 2008 via www.webmd.com/rheumatoid-arthritis/tc/rheumatoid-arthritis-prevention, dated on Aug. 23, 2006.

Tseng et al., "Heterogeneity of Saturable Estradiol Binding Sites in Nuclei of Human Endometrium. Estetrol Studies", (1978), vol. 9, pp. 1145-1148.

Fishman et al., "Fate of 15 α-Hydroxyestriol-3H in Adult Man", J. Clin. Endocrinol. Metab., (1970), vol. 31, pp. 436-438.

Levine et al., "Uterine vascular effects of estetrol in nonpregnant ewes", Am. J. Obstet. Gynecol., (1984), [148], vol. 73, pp. 735-738.

Martucci et al., "Direction of Estradiol Metabolish as a Control of its Hormonal Action—Uterotrophic Activity of Estradiol Metabolites", Endocrin., (1977), vol. 101, pp. 1709-1715.

Martucci et al., "Uterine Estrogen Receptor Binding of Catecholestrogens and of Estetrol (1,3,5(10)-Estratriene-3, 15a, 16a, 17 β-Tetrol)", Steroids, (1976), vol. 27, pp. 325-333.

Seeger et al., "The inhibitory effect of endogenous estrogen metabolies on copper-mediated in vitro oxidation of LDL", Int. Journal of Clinical Pharmacology and Therapeutics, (1998), vol. 36, No. 7, pp. 383-385.

Tseng et al., "Competition of Estetrol and Ethynylestradiol with Estradiol for Nuclear Binding in Human Endometrium", Journal of Steroid Biochemistry, (1976), vol. 7, pp. 817-822.

Kuipers et al., "Enterohepatic Circulation in the Rat", Gastroenterol., vol. 88, pp. 403-411 (1985).

Schwartz, "A Model for the Regulation of Ovulation in the Rat", Recent Prog. Horm. Res., vol. 25, pp. 1-55, (1969).

Beattie et al., "The Differential Effects of Diestrous Progestogen Administration on Proestrous Gonadotrophin Levels, Endocrinol", vol. 97, pp. 885-890, (1975).

De Visser et al., Endocrinological Studies with (7a, 17 a)-17-Hydroxy-7-me norpregn-5(10)-en-20-yn-3-one (Org OD 14), Arzneim, Forsh., vol. 34, pp. 1010-1020, (1984).

National Cancer Institute: Breast cancer prevention retrieved online Aug. 7, 2007 from the internet; http://www.cancer.gov/templates/doc.aspx?viewed+D972A74B-D25A-4F86-B8ED-33EB3C0450E4 &version, p. 1.

Medline Plus: Medical Encyclopedia: Ovarian cancer retrieved online on Aug. 9, 2007 from the internet: https://www.nlm.nih.gov/medlineplus/ovariancancer.html, p. 1 dated Jul. 31, 2007.

Coelingh-Bennink et al., "Estetrol review: profile and potential clinical applications", International Menopause Society, Climateric, vol. 11, (Suppl 1), pp. 47-58 (2008).

Speroff et al., Clinical Gynecologic Endocrinology and Infertility, Seventh Edition, p. 270 (partial), 2005.

White et al., "The pharmacokinetics of Intravenous Estradiol: A Preliminary Study", Pharmacotherapy, vol. 18, pp. 1343-1346, (1998) (Abstract).

Hammond et al., "Estetrol does not bind sex hormone binding globulin or increase its production by human HepG2 cells", International Menopause Society, Climateric, vol. 11, (Suppl. 1), pp. 41-46, (2008).

* cited by examiner

METHOD OF TREATING HUMAN SKIN AND A SKIN CARE COMPOSITION FOR USE IN SUCH A METHOD

FIELD OF THE INVENTION

The present invention relates to a cosmetic method of treating human skin by delivering an estrogenic component to said skin. More particularly, the invention is concerned with such a method that comprises applying to the skin a composition containing an estrogenic component and a cosmetically acceptable vehicle.

Another aspect of the invention concerns a method of therapeutic method of treating or preventing vaginal dryness or acne and a therapeutic method of promoting wound healing, which methods comprise the delivery of an estrogenic component to vaginal or skin epithelium.

Yet another aspect of the invention relates to a skin care composition comprising an estrogenic component and a cosmetically acceptable vehicle.

BACKGROUND OF THE INVENTION

The human skin consists of two major layers, the bottom thicker layer (dermis) and the top thinner layer (epidermis). Dermis is the layer which provides the strength, elasticity and the thickness to the skin.

The main cell type of the dermis is the fibroblast, which is responsible for synthesis and secretion of all the dermal matrix components such as collagen, elastin and glycosaminoglycans. Collagen provides the strength, elastin the elasticity and glycosaminoglycans the moistness and plumpness of the skin. With ageing, the thickness of the dermal layer is reduced and this is believed to be partially responsible for the formation of wrinkles in ageing skin. The top layer of human skin or the epidermis which provides the resilience and the barrier properties of the skin, is composed of many different cell types including keratinocytes, melanocytes and langerhans cells. Keratinocyte is the major cell type of the epidermis (75-80% of the total number of cells in the human epidermis). Richards et al. reported that estrogen stimulates secretion of a protein, prolactin, by human dermal fibroblast cells and that prolactin then stimulates proliferation of keratinocytes (Richards et al., Human Dermal Fibroblasts Express Prolactin In Vitro., J. Invest. Dermatol. (1996), 106: 1250).

Estrogens and synthetic compounds which act like estrogens are known to increase the thickness of the dermal layer and to reduce wrinkle formation in the ageing skin. The changes in the skin such as skin dryness, loss of skin elasticity and plumpness occurring after menopause is attributed to the lack of estrogen production. Estrogen therapy prevents or slows down many of these changes associated with ageing skin (Creidi et al., "Effect of a conjugated estrogen cream on ageing facial skin", Maturitas, (1994) 19, p. 211). Some of the effects of estrogen on skin include: increase in skin thickness and disappearance of fine wrinkles, increase of the mitotic rate of the epidermis, reduction in the size and activity of the sebaceous gland, slow down of the rate of hair growth, stimulation of collagen turnover and increase in the production of hyaluronic acid and glycosaminoglycan synthesis of the fibroblasts (Pugliese, Menopausal skin, Skin Inc., March/April 1994: p 69-77).

Schmidt et al. report on the effects on ageing skin of the face of perimenopausal females treated with a 0.3% estriol cream or with a 0.01% estradiol cream for 6 months (Schmidt et al., "Treatment of skin ageing symptoms in perimenopausal females with estrogen compounds. A pilot study", Maturitas (1994), 29(1), 25-30). Both treatment groups were found to show improvement of the various skin ageing symptoms at the end of treatment. The effects of the group treated with topical estriol were deemed to be slightly superior with regard to their extent and onset.

Shah et al. ("Estrogen and skin. An overview", Am J Clin Dermatol (2001); 2(3):143-150) report that topical and systemic estrogen therapy can increase the skin collagen content and therefore maintain skin thickness. In addition, it is said that estrogen maintains skin moisture by increasing acid mucopolysaccharides and hyaluronic acid in the skin and possibly maintaining stratum corneum barrier function. Furthermore it is observed that estrogen may increase cutaneous wound healing by regulating cytokine levels as topical estrogen has been found to accelerate and improve wound healing in elderly men and women.

In a review article by Sitruk-Ware et al. ("Topical hormonal treatment and urogenital atrophy", Schweiz Rundsch Med Prax (1997) August 13; 86(33):1245-1248) it is stated that local estrogen therapies are recommended for the treatment of complaints due to vulvar and vaginal atrophy. Estrogens specifically mentioned in the review article include estrone, promestriene, estradiol and estriol.

SUMMARY OF THE INVENTION

The present invention provides a particularly effective method of improving or preventing the condition of wrinkled, lined, dry, flaky, aged or photodamaged skin and of improving skin thickness, elasticity, flexibility and plumpness, which method includes applying to the skin a composition that contains an estrogenic component and a cosmetically acceptable carrier. The present invention encompasses a cosmetic method of increasing fibroblast and epidermal skin cell proliferation in human skin by applying to the skin the inventive composition. The present method may be applied to human skin which is already dry, flaky, lined, wrinkled, aged, photodamaged, or to healthy skin to prevent or reduce such deteriorative changes. The invention also concerns a therapeutic method of treating or preventing vaginal dryness as well as a method of promoting wound healing, which methods comprise the delivery of the composition as described herein before to the vaginal or skin epithelium.

The inventors have unexpectedly found that topical application of a special group of estrogenic substances produces surprisingly good results in terms of elasticity and firmness of the skin, wrinkle depth and pore sizes and/or skin moisture. These special estrogenic substances are represented by the following formula

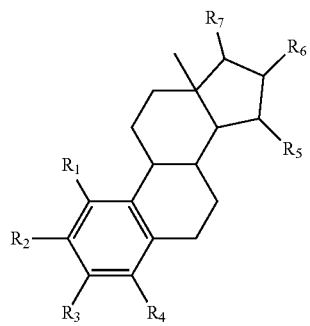

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms.

A known representative of this group of estrogenic substances is 1,3,5(10)-estratrien-3, 15α,16α,17β-tetrol, also known by the names of estetrol, oestetrol and 15α-hydroxyestriol. Estetrol is an estrogen that is produced by the fetal liver during human pregnancy. Unconjugated estetrol levels in maternal plasma peak at about 1.2 ng/ml at term pregnancy and are about 12 times higher in fetal than in maternal plasma (Tulchinsky et al., 1975. J. Clin. Endocrinol. Metab., 40, 560-567).

In 1970, Fishman et al., "Fate of 15α-hydroxyestriol-³H in Adult Man", J Clin Endocrinol Metab (1970) 31, 436-438, reported the results of a study wherein tritium labeled 15α-hydroxyestriol (estetrol) was administered intravenously to two adult women. It was found that the estetrol was rapidly and completely excreted in urine as the glucosiduronate and that virtually no metabolism except for conjugation took place.

Between 1975 and 1985 several researchers have investigated the properties of estetrol and reported on its estrogenic potency and uterotrophic activity. The most relevant publications that were issued during this period are mentioned below:

Levine et al., 1984. Uterine vascular effects of estetrol in nonpregnant ewes. Am. J. Obstet. Gynecol., 148:73, 735-738: "When intravenously administered in nonpregnant ewes, estetrol is 15 to 30 times less potent than estriol and 17β-estradiol in uterine vasodilation".

Jozan et al., 1981. Different effects of oestradiol, oestriol, oestetrol and of oestrone on human breast cancer cells (MCF-7) in long term tissue culture. Acta Endocrinologica, 98, 73-80: "Estetrol agonistic potency is 2% of the magnitude observed for 17β-estradiol in in vitro cell proliferation".

Holinka et al., 1980. Comparison of effects of estetrol and tamoxifen with those of estriol and estradiol on the immature rat uterus. Biol. Reprod. 22, 913-926: "Subcutaneously administered estetrol has very weak uterotrophic activity and is considerable less potent than 17β-estradiol and estriol".

Holinka et al., 1979. In vivo effects of estetrol on the immature rat uterus. Biol. Reprod. 20, 242-246: "Subcutaneously administered estetrol has very weak uterotrophic activity and is considerable less potent than 17β-estradiol and estriol".

Tseng et al., 1978. Heterogeneity of saturable estradiol binding sites in nuclei of human endometrium. Estetrol studies. J. Steroid Biochem. 9, 1145-1148: "Relative binding of estetrol to estrogen receptors in the human endometrium is 1.5% of 17β-estradiol".

Martucci et al., 1977. Direction of estradiol metabolism as a control of its hormonal action-uterotrophic activity of estradiol metabolites. Endocrin. 101, 1709-1715: "Continuous administration of estetrol from a subcutaneous depot shows very weak uterotrophic activity and is considerably less potent than 17β-estradiol and estriol".

Tseng et al., 1976. Competition of estetrol and ethynylestradiol with estradiol for nuclear binding in human endometrium. J. Steroid Biochem. 7, 817-822: "The relative binding constant of estetrol binding to the estrogen receptor in the human endometrium is 6.25% compared to 17β-estradiol (100%)".

Martucci et al., 1976. Uterine estrogen receptor binding of catecholestrogens and of estetrol (1,3,5(10)-estratriene-3,15alpha,16alpha,17beta-tetrol). Steroids, 27, 325-333: "Relative binding affinity of estetrol to rat uterine cytosol estrogen receptor is 0.5% of 17,β-estradiol (100%). Furthermore, the relative binding affinity of estetrol to rat uterine nuclear estrogen receptor is 0.3% of 17β-estradiol (100%)".

All of the above publications have in common that the authors have investigated the estrogenic potency of estetrol. Without exception they all conclude that estetrol is a weak estrogen. In some of the cited articles the estrogenic potency of estetrol has been found to be much lower than that of a relatively weak estrogen that is commonly used in pharmaceutical formulations, namely 17β-estradiol With these findings in mind, it is not surprising that the interest in estetrol has dwindled since the early eighties and that no publications on the properties of estetrol have been issued since.

In view of the low estrogenic potency of the estetrol-like substances that are employed in the present method, it is surprising that these substances may effectively be used in the treatment of human skin. Although the inventors do not wish to be bound by theory, it is believed that this efficacy may be related to the ability of the these substances to penetrate through the skin and the relatively high in vivo half-life of these substances in comparison to e.g. 17β-estradiol and estriol.

DETAILED DESCRIPTION OF THE INVENTION

One aspect of the invention concerns a cosmetic method of treating human skin by delivering an estrogenic component to said skin, the method comprising applying to the skin a composition containing:
(i) at least 5 µg/g of an estrogenic component selected from the group consisting of: substances represented by the following formula

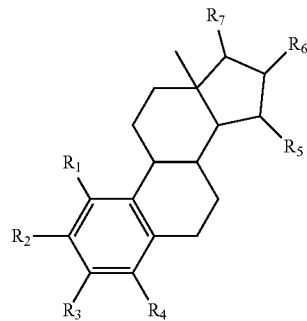

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms;
precursors capable of liberating a substance according to the aforementioned formula when used in the present method; and
mixtures of one or more of the aforementioned substances and/or precursors; and
(ii) a cosmetically acceptable vehicle.

The term "estrogenic component" as used throughout this document encompasses substances that are capable of triggering an estrogenic response in vivo, as well as precursors that are capable of liberating such an estrogenic component in vivo when used in accordance with the present invention. In order for estrogenic components to trigger such a response they normally have to bind to an estrogen receptor, which receptors are found in various tissues within the mammalian body. It is noted that the present invention not only encompasses the use of estrogenic substances specifically mentioned in this application, but also metabolites of these hormones that display comparable in vivo functionality. In this context it is observed that, for instance, estriol is a metabolite of 17β-estradiol.

The terminology "delivering the estrogenic component to the skin" relates to the application of said estrogenic component to the surface of the skin, in particular topical application or transdermal application. Topical application suitably includes the application of e.g. salves, lotions and creams to the skin surface. Transdermal application encompasses the fixation to the skin epithelium of transdermal patches that contain the present composition.

An important benefit of the present method resides in the ability of the present estrogenic components to enhance proliferation of fibroblasts and/or epidermal cells. Consequently, in a preferred embodiment, the present composition is applied in an effective amount to enhance proliferation of fibroblasts and/or epidermal skin cells. Enhanced proliferation will induce a "rejuvenation" of the skin as demonstrated by increased elasticity and firmness of the skin, reduced wrinkle depth and pore sizes and/or increased skin moisture.

On a macroscopic level the benefits of the present method manifest themselves in the form of improved skin thickness and/or skin elasticity, provided the composition is applied in an effective amount. A particularly preferred embodiment of the present invention relates to a cosmetic method, wherein the present composition is applied in an effective amount to improve or prevent the condition of wrinkled, lined, dry, flaky, aged or photodamaged skin.

Although the present invention is perfectly suitable for treating hypoestrogenic subjects, e.g. (peri-)menopausal and post-menopausal females, it is preferred not to apply the present estrogenic component to the skin in sufficient quantities to significantly suppress symptoms of hypoestrogenism, such as osteoporosis and climacteric symptoms (e.g. hot flushes, palpitations and mood disturbances). The latter symptoms of hypoestrogenism are more effectively treated by e.g. oral or subcutaneous administration.

The present estrogenic substances are distinct from both the estrogens that are commonly applied in pharmaceutical formulations (e.g. 17α-ethinyl estadiol and 17β-estradiol) in that they contain at least 4 hydroxyl groups. The present substances are particularly special in that the 5 membered ring in the steroid skeleton comprises 3 hydroxyl substituents rather than 0-2.

Known estrogens that contain at least 4-hydroxyl groups and derivatives thereof are:
1,3,5(10)-estratrien-2,3,15α,16α,17β-pentol 2-methyl ether
1,3,5(10)-estratrien-2,3,15β,16α,17β-pentol 2-methyl ether
1,3,5(10)-estratrien-2,3,16α,17β-tetrol
1,3,5(10)-estratrien-3,4,16α,17β-tetrol 4-methyl ether
1,3,5(10)-estratrien-3,15α,16α,17β-tetrol
1,3,5(10)-estratrien-3,15α,16α,17β-tetrol tetra acetate
1,3,5(10)-estratrien-3,15β,16β,17β-tetrol tetra acetate Preferably, the estrogenic substance applied as the active component in the present composition is a so called biogenic estrogen, i.e. an estrogen that occurs naturally in the human body, or a precursor thereof. Because biogenic estrogens are naturally present in the fetal and female body, side-effects are not expected to occur, particularly not if the serum levels resulting from the exogenous administration of such estrogens do not exceed naturally occurring concentrations. Since estetrol serum levels in the fetus are several times higher than those found in pregnant females and knowing that the fetus is particularly vulnerable, estetrol is deemed to be a particularly safe biogenic estrogen.

In a preferred embodiment of the present invention the estrogenic substance contains 4 hydroxyl groups. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The estrogenic substances according to the formula encompass various enantiomers since the carbon atoms that carry hydroxyl-substituents $R_5$, $R_6$ and $R_7$ are chirally active. In one preferred embodiment, the present estrogenic substance is 15α-hydroxy substituted. In another preferred embodiment the substance is 16α-hydroxy substituted. In yet another preferred embodiment, the substances is 17β-hydroxy substituted. Most preferably the estrogenic substances are 15α,16α,17β-trihydroxy substituted.

In another preferred embodiment of the present invention $R_3$ represents a hydroxyl group or an alkoxy group. In another preferred embodiment the groups $R_1$, $R_2$ and $R_4$ represent hydrogen atoms, in which case, if $R_3$, $R_5$, $R_6$ and $R_7$ are hydroxyl groups, the substance is 1,3,5(10)-estratrien-3,15, 16,17-tetrol. A preferred isomer of the latter substance is 1,3,5(10)-estratrien-3,15α,16α,17β-tetrol (estetrol).

The invention also encompasses the use of precursors of the estrogenic substances that constitute the active component in the present method. These precursors are capable of liberating the aforementioned estrogenic substances when used in the present method, e.g. as a result of metabolic conversion. These precursors are preferably selected from the group of androgenic precursors as well as derivatives of the present estrogenic substances. Suitable examples of androgenic precursors include androgens that can be converted into the present estrogenic substances through in vivo aromatisation. Examples of derivatives of the present estrogenic substances that can suitably be used as precursors include such substances wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranal; or a straight or branched chain glycosydic residue containing 1-20 glycosidic units per residue.

Typical examples of precursors which can suitably be used in accordance with the invention are esters that can be obtained by reacting the hydroxyl groups of the estrogenic substances with substances that contain one or more carboxy ($M^+$—OOC—) groups, wherein $M^+$ represents a hydrogen or (akali)metal cation. Hence, in a particularly preferred embodiment, the precursors are derivatives of the estrogenic substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The composition that is applied to the skin in accordance with the present invention suitably contains at least 10 μg/g of the estrogenic component. Particularly satisfactory results can be obtained if the composition contains at least 30 μg/g, more preferably at least 50 μg/g and most preferably at least 100 μg/g of the estrogenic component. For practical reasons the present composition will usually not contain more than 50 mg/g of the estrogenic component. Preferably said composition contains not more than 20 mg/g, more preferably not more than 10 mg/g of the estrogenic component.

The advantages of the present invention may be realised in skin as it is found in different places of the human body. Particularly advantageous results can be obtained by applying the composition to e.g. face, neck, shoulders, breast, buttocks (cellulitis) etc. In a preferred embodiment of the present method, the skin care composition is applied to facial skin or the skin of the neck.

In order to obtain quick and lasting results it is advisable to apply the present composition at least once a day during a period of at least 3 days, particularly in case of topical application. Because transdermal application enables the relatively slow release of the present estrogenic component over a longer period of time, transdermal application is preferably carried out with a frequency of at least once a week. Topical application of the estrogenic component is the preferred mode of administration as it is uncomplicated, effective and produces essentially no undesirable side-effects.

The topical application of the present composition is preferably carried out in such a way that virtually all of the composition that has been applied to the skin, is allowed to penetrate said skin. When applied topically, a small quantity of the present composition, for example from 0.1 to 100 g, is applied directly to the skin, optionally from a suitable container or applicator and, if necessary, it is then spread over and/or rubbed into the skin using the hand or fingers or a suitable device.

The benefits of the present invention are most pronounced when the composition is applied in the course of a longer term treatment. Therefore, the present method, preferably, comprises administering the estrogenic component for a period of at least 1 week, more preferably of at least 3 weeks. The present method usually employs uninterrupted administration of the estrogenic component during at least 10, preferably at least 20 days. The term "uninterrupted" as used in here, means that the estrogenic component is administered at relatively regular intervals, with no (therapeutically) significant interruptions. Naturally, minor interruptions may occur that do not affect the overall effectiveness of the present method, and indeed such aberrations are encompassed by the present invention. In a preferred embodiment, and more arithmetically, the administration regimen is deemed to be uninterrupted if the longest interval between 2 subsequent administrations is not more than 3.5 times as long as the average interval. Even more preferably said longest interval is not more than 2.5 times, most preferably not more than 1.5 times as long as the average interval.

Another aspect of the invention relates to a method of treating or preventing vaginal dryness, wherein the method comprises applying to the vaginal epithelium a composition containing:
(i) at least 5 μg/g of the present estrogenic component; and
(ii) a cosmetically acceptable vehicle.

A further aspect of the invention relates to a method of promoting wound healing, wherein the method comprises applying to the wounded tissue or to tissue in the vicinity of the wound a composition containing:
(i) at least 5 μg/g of said estrogenic component; and
(ii) a cosmetically acceptable vehicle.

Yet another aspect of the invention relates a method of treating or preventing acne, wherein the method comprises applying to the skin that is affected by acne or that is at risk of being affected by acne a composition containing:
(i) at least 5 μg/g of said estrogenic component; and
(ii) a cosmetically acceptable vehicle.

The preferred embodiments discussed herein before in relation to the treatment of skin equally apply to the present method of treating or preventing vaginal dryness and the method of promoting wound healing. In the latter methods continuous administration of the present composition during prolonged periods of time may not be necessary, particularly not in case of wound healing. Indeed, the present method of promoting wound healing and, to a lesser extent, the method of treating vaginal dryness may suitably employ administration on demand.

Yet another aspect of the invention relates to a skin care composition for topical administration, in accordance with the method described herein before, said composition containing:
(i) at least 5 μg/g of the estrogenic component; and
(ii) a cosmetically acceptable vehicle.

The composition according to the invention comprises a cosmetically acceptable vehicle to act as a diluant, dispersant or carrier for the estrogenic component, so as to facilitate its distribution when the composition is applied to the skin. Vehicles other than or in addition to water can include liquid or solid emollients, solvents, humectants, thickeners and powders. Particularly suitable nonaqueous carriers include polydimethyl siloxane and/or polydimethyl phenyl siloxane. Especially desirable are mixtures of low and high viscosity silicones. These silicones are available from the General Electric Company under trademarks Vicasil, SE and SF and from the Dow Corning Company under the 200 and 550 Series. The amounts of silicone which can be utilised in the compositions of this invention can range anywhere from 5% to 95%, preferably from 25% to 90% by weight of the composition. The cosmetically acceptable vehicle will usually form from 5% to 99.9%, preferably from 25% to 95% by weight of the composition, and can, in the absence of other cosmetic adjuncts, form the balance of the composition. Preferably, the vehicle is at least 80 wt. % water. Preferably, water constitutes at least 50 wt. % of the present composition, most preferably from 60 to 80 wt. %, by weight of the composition.

The skin care composition of the present invention may contain an oil or lipid material, together with an emulsifier, to provide either a water-in-oil emulsion or an oil-in-water emulsion, depending largely on the average hydrophilic-lipophilic balance (HLB) of the emulsifier employed. The present compositions include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Emollients can advantageously be incorporated into the compositions of the present invention. Levels of such emollients may range from 0.5% to 50%, preferably from 5% and 30% by weight of the total composition. Emollients may be classified under such general chemical categories as esters, fatty acids and alcohols, polyols and hydrocarbons. Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate. Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers. Exemplary hydrocarbons which may serve as emollients are those having hydrocarbon chains anywhere from 12 to 30 carton atoms. Specific examples include mineral oil, petroleum jelly, squalene and isoparaffins.

Another category of functional ingredients that may be employed in the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may also be incorporated into the composition of the invention. These powders include chalk, talc, kaolin, starch, smectite clays, chemically modified magnesium aluminium silicate, organically modified montmorillonite clay, hydrated aluminium silicate, fumed silica, aluminium starch octenyl succinate and mixtures thereof.

Other adjunct minor components may also be incorporated into the present compositions. These ingredients may include colouring agents, opacifiers and perfumes. Amounts of these other adjunct minor components may range anywhere from 0:001% up to 20% by weight of the composition.

The topical skin care composition of the invention can be formulated e.g. as a lotion, a cream or a salve (e.g. a gel). The composition can be packaged in a suitable container to suit its viscosity and intended use by the consumer. For example, a lotion or a cream can be packaged in a bottle or a roll-ball applicator, or a propellant-driven aerosol device or a container fitted with a pump suitable for finger operation. When the composition is a cream or a salve, it can simply be stored in a non-deformable bottle or squeeze container, such as a tube or a lidded jar. The composition may also be included in capsules such as those described in U.S. Pat. No. 5,063,507, incorporated by reference herein. The invention accordingly also provides a closed container containing a cosmetically acceptable composition as herein defined.

The present invention is further illustrated by the following examples, which, however, are not to be construed as limiting. The features disclosed in the foregoing description, in the following examples and in the claims may, both separately and in any combination thereof, be material for realising the invention in diverse forms thereof.

EXAMPLES

Example 1

Established competitive steroid binding assays were used to determine the relative binding affinity of estetrol (E4), as compared to 17α-ethinylestradiol(EE) and 17β-estradiol (E2), to human Estrogen Receptor (ER) α- and β-forms.

The method employed was adapted from the scientific literature and described in detail by Osbourn et al. (1993, Biochemistry, 32, 6229-6236). Recombinant human ERα and ERβ proteins were purified from transfected Sf9-cells. The in vitro assays involved the use of either ERα or ERβ proteins and [$^3$H]E2, at a fixed concentration of 0.5 nM, as the labeled ligand. Recombinant human ERα or ERβ proteins were dissolved in binding buffer (10 mM Tris-HCL, pH 7.5, 10% glycerol, 1 mM DTT, 1 mg/ml BSA) and duplicate aliquots were then incubated with [$^3$H]E2 at a final concentration of 0.5 nM, together with a vehicle control (0.4% DMSO), or the same amount of vehicle containing increasing concentrations of unlabeled steroid ligands as competitors. After incubation for 2 h at 25° C., the unbound ligands were removed and the amounts of [$^3$H]E2 bound to either ERα or ERβ proteins were measured. The average amounts of [$^3$H]E2 bound to either ERα or ERβ proteins at each concentration of competitor were used to make inhibition curves. IC50 values were subsequently determined by a non-linear, least squares regression analysis. Inhibition constants (Ki) were calculated using the equation of Cheng and Prusoff (Cheng et al., 1973, Biochem. Pharmacol., 22, 3099-3108), using the measured IC50 of the tested compounds, the concentration of radioligand employed in the assay, and the historical values for the Kd of the radioligand, which were established as 0.2 nM and 0.13 nM for ERα and ERβ, respectively.

Biochemical assay results for E4 are presented as the percent inhibition of specific binding in three separate experiments (Table 1). For comparision of binding affinities of E4, EE and E2 to human ERα and ERβ proteins, experimentally observed Ki values are shown in Table 2. As compared to both EE and E2, E4 shows substantially less bind affinity for ERα and ERβ receptor forms (Table 2).

TABLE 1

Percent inhibition of specific binding to ERα and ERβ proteins using E4 as unlabeled steroid ligand and 0.5 nM [3H] as labeled competitor. Results of three separate experiments are shown.

| | Percent inhibition of specific binding in | | | | | |
|---|---|---|---|---|---|---|
| E4 final | ERα steroid binding assay | | | ERβ steroid binding assay | | |
| concentration | Test 1 | Test 2 | Test 3 | Test 1 | Test 2 | Test 3 |
| 1 μM | 98 | nd | nd | 87 | 90 | 95 |
| 0.3 μM | 92 | 94 | 101 | 74 | 74 | 77 |
| 0.1 μM | 83 | 85 | 86 | 56 | 54 | 50 |
| 0.03 μM | 64 | 66 | 63 | 19 | 25 | 30 |
| 10 nM | 43 | 32 | 28 | nd | nd | nd |
| 3 nM | 26 | 17 | 11 | nd | nd | nd | nd: not determined

TABLE 2

Experimentally determined inhibition constants (Ki) for estetrol (E4), 17α-ethinylestradiol (EE) and 17β-estradiol (E2), to human ERα and ERβ proteins.

| Steroid ligands | Ki ERα (nM) | Ki ERβ (nM) |
|---|---|---|
| EE | 0.23 | 0.025 |
| E2 | 0.21 | 0.015 |
| E4 | 4.9 | 19 |

Example 2

To determine the in vivo stability of estetrol (E4) its elimination half-life in female Sprague Dawley rats was determined after a single subcutaneous administration (sc) at several dose levels.

Female Sprague Dawley rats were equipped with a permanent silatic heart catheter, as described by Kuipers et al. (1985, Gastroenterology, 88, 403-411). Rats were allowed to recover from surgery for 5 days and were than administered 0.05, 0.5, or 5 mg/kg E4 in 0.5 ml arachidis oil. E4 was injected in the neck area using a 1 ml syringe and 20 g needle. Blood samples were subsequently collected via the heart catheter in heparinized tubes at 0.5, 1, 2, 4, 8 and 24 hours. Erythrocytes were removed by centrifugation at 5000×g for 10 minutes at 4° C. and blood plasma was stored at −20° C. After thawing the plasma samples, liquid-liquid extraction (hexane and diethyl ether) was employed to prepare the E4-containing plasma samples for HPLC analysis (Perkin Elmer 200) and tandem mass spectrometry using a PE Sciex 3000 tandem mass spectrometer and APCI interface. With each sample batch, a calibration curve with 6 calibrators was recorded. The calibration curve was calculated using linear regression (correlation coefficient>0.98), which permitted quantitation of plasma concentrations. For each rat plasma, sampled at different time intervals, data were collected.

Plasma E4 concentration data were analysed with "WinNonLin, edition 3.1" and involved pharmacokinetic parameters for $C_{max}$, $AUC_{0-24}$ and half-life. Interestingly, E4 demonstrated good stability with a relatively long half-life of 2-3 hours, enabling the detection of bioactive levels of unconjugated E4 at all time points over a 24 hour interval.

Example 3

Preparation of a Skin Cream Containing 1 mg/g Estetrol.
A. Preparation of the Cream:
  I. Boil in a beaker 60 ml purified water. Stop heating and add 4 grams solutio sorbitoli and 0.2 gram acidum sorbicum and dissolve completely. Cover the beaker and cool down until 70° C.
  II. Simultaneously heat 15 grams Cera cetomacrogolis emulsificans together with 20 grams of Cetiol V until 70° C.
  Mix I and II by stirring gently and allow the cream to cool down (under occasional stirring). Add purified (boiled) water until 100 gram under stirring.
B Preparation of the Cream Containing Estetrol:
  Take 99.9 grams of the cream, as described under A, and add 100 mg of estetrol under stirring. Continue stirring until the estetrol has been homogeneously dispersed throughout the cream.

Example 4

Twenty women, who are post-menopausal and in good health, are selected on the basis of presenting several signs of rapid dermal atrophy, such as a rapid increase in the number of facial wrinkles or crow's feet, rapid change in the pigmentation of the skin, i.e. "age spots", or other complaints of rapid dermal ageing. Since dermal atrophy may also be the result of other factors such as UV damage from the sun or other environmental insults, consideration is taken to exclude patients, who are suffering from these effects, from the clinical study.

The first component of the study is qualitative by making an evaluation of improvement in the patient's appearance. This evaluation requires a baseline level for future comparison. An initial baseline value is created in the form of a standardised set of questions as to how the patient views her own appearance, photographs of the patient, and a psychological profile of the patient's self-image. The second component is quantitative, including the measurement of urinary excretion of hydroxyproline, moisture content of the skin, glycosaminoglycans in the skin, and changes in resilience and pliability of the skin. Methods for determining these factors are found in "The Menopause", Ed. R. J. Beard, University Press, Chapter 7 (1977) and "Methods in Skin Research", Ed. Skerrow, D. and Skerrow C. J., John Wiley & Sons Ltd., Chp. 22, "Analysis of Sebaceous Lipids", p. 587-608 (1985), and further references cited therein, all herein incorporated by reference. Again, before the start of the study baseline values of these quantitative factors are obtained.

The study volunteers are subsequently placed in a clinical protocol receiving the topical compound formulation as set forth in example 3. The compound formulation is administered to areas of the skin most effected by atrophy twice a day, which is continued for 1 to 3 months. Evaluations, both quantitative and qualitative, are made at biweekly intervals.

The compound formulation, as set forth in example 3 gives positive results in a majority of participating study subjects by improving the overall qualitative index of the patient's appearance and/or the quantitative parameters, e.g., an increase in the urinary excretion of hydroxyproline signifying an increase in turnover and synthesis of collagen, an increase in moisture content, glycosaminoglycans, pliability, or resilience of the skin.

Example 5

Twenty women suffering from vaginal atrophy and/or vaginal dryness symptom associated with menopause are selected. These women are in general good health. Since the nature of this disorder is highly subjective, evaluation of the effectiveness of treatment is necessarily also subjective in nature. The female subjects are asked to keep a daily log, noting details as to the degree of vaginal itching, dryness and dyspareunia, and to use a visual analogue scale to record their subjective estimates. The change from pretreatment (base line value) during 1 to 3 months of treatment is assessed and considered to be indicative of the treatment efficacy.

The study volunteers subsequently participate in a clinical protocol receiving the topical compound formulation as set forth in example 3. The compound formulation is administered intravaginally once a day, which is continued for 1 to 3 months. Evaluations of vaginal itching, dryness and dyspareunia are made at biweekly intervals. Utility of estetrol is demonstrated by the positive results observed in a majority of participating study subjects showing improvements in qualitative change from baseline value for vaginal itching, dryness and dyspareunia.

Example 6

Wound Care Ointment Containing 1 mg/g Estetrol

Heat together 2.5 grams alcohol cetostearliylicus, 6 gram adeps lanae, 51.5 gram vaselinum album and 40 grams paraffinum liquidum until all ingredients are melted. The warm mixture is filtered using a paper filter. The filtered mixture is subsequently sterilised using a 0.2 micrometer filter.

100 mg estetrol is thoroughly mixed with 99.9 gram of the above described ointment under aseptic conditions.

The invention claimed is:
1. A method of treating or reducing a risk of developing vaginal dryness, wherein the method comprises applying to the vaginal epithelium a composition containing:
   (i) at least 5 µg/g of an estrogenic component selected from the group consisting of: estetrol,
precursors capable of liberating estetrol when used in the present method, wherein the precursors are derivatives of estetrol;

wherein the hydrogen atom of at least one of the hydroxyl groups has been substituted by —CO—R; wherein R is hydrogen or an alkyl, alkenyl or aryl radical comprising 1-20 carbon atoms; and mixtures of estetrol and the precursors; and (ii) a cosmetically acceptable vehicle.

2. The method according to claim 1, wherein the composition contains at least 10 μg/g of the estrogenic component.

3. The method according to claim 1, wherein the composition is applied at least once a day during a period of at least 3 days.

4. The method according to claim 1, which composition is a lotion, salve or a cream.

5. The method according to claim 1, wherein the method is for treating vaginal dryness.

* * * * *